US012740925B2

(12) United States Patent
Chiou et al.

(10) Patent No.: US 12,740,925 B2
(45) Date of Patent: Sep. 22, 2026

(54) COMPOSITIONS AND ARTICLES FOR MAKE-UP REMOVAL

(71) Applicant: L'OREAL, Paris (FR)

(72) Inventors: Catherine Chiou, Saddlebrook, NJ (US); Ryuji Hara, Westfield, NJ (US); Jean-Pascal Hirt, Saint Cloud (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/422,976

(22) Filed: May 25, 2019

(65) Prior Publication Data

US 2020/0368558 A1 Nov. 26, 2020

(51) Int. Cl.

*A61K 8/02* (2006.01)
*A61K 8/49* (2006.01)
*A61K 9/00* (2006.01)
*A61Q 1/14* (2006.01)
*A61Q 19/10* (2006.01)

(52) U.S. Cl.

CPC .............. *A61K 8/0208* (2013.01); *A61K 8/49* (2013.01); *A61K 9/0014* (2013.01); *A61Q 1/14* (2013.01); *A61Q 19/10* (2013.01)

(58) Field of Classification Search

None

See application file for complete search history.

(56) References Cited

U.S. PATENT DOCUMENTS 4,690,818 A * 9/1987 Puchalski, Jr. ........ A61K 8/042 424/70.14
5,585,104 A * 12/1996 Ha .......................... A61K 8/06 424/401
5,993,792 A * 11/1999 Rath ....................... A61K 8/31 424/400
6,730,621 B2 * 5/2004 Gott ..................... A61K 8/0208 442/123
6,762,158 B2 7/2004 Lukenbach et al.
7,262,158 B1 8/2007 Lukenbach et al.
2002/0015684 A1 * 2/2002 Vatter ...................... A61K 8/92 424/70.12
2004/0013859 A1 * 1/2004 Annis .................. A61K 8/0208 428/195.1
2005/0238605 A1 * 10/2005 Kohlhase ............... A61K 8/375 424/70.13
2007/0178144 A1 8/2007 Hameyer et al.
2011/0088711 A1 4/2011 Bonafos
2013/0310530 A1 11/2013 Jha et al.
2019/0336407 A1 * 11/2019 Figueroa ................. A61K 8/31

FOREIGN PATENT DOCUMENTS

CN 101795612 A 8/2010
CN 106163494 A 11/2016
JP 2003517882 6/2003
JP 2005145872 6/2005
JP 2008184413 A 8/2008
JP 2015030682 2/2015
JP 2016190819 11/2016
WO 0145615 A1 6/2001

OTHER PUBLICATIONS

Database GNPD Mintel; Dec. 11, 2018 (Dec. 11, 2018), anonymous: "Make Up Remover Wipes", XP055710026, retrieved from www.gnpd.com.
Database GNPD Mintel; May 11, 2018 (May 11, 2018), anonymous: "Dark Bierries Facial Cleansing Wipes", XP055710034, retrieved from www.gnpd.com.
International Search Report for PCT/US2020/033513, dated Jul. 9, 2020.
Examination Report issued to European counterpart Application No. 20732352.8 dated Jan. 3, 2024.
Anonymous, Mintel, "One-Step Aloe Makeup Removing Wipes," record ID 3883921, Mar. 2016, www.gnpd.com.
Anonymous, Mintel, "2go Perfect Clea Make-up Remover Wipes," record ID 4696657, Mar. 2017, www.gnpd.com.
Search Report issued to Chinese counterpart Application No. 202080030818.1 dated May 16, 2023.
Anonymous, Mintel, "Daily Care Grape Water Gentle Cleansing Milk," ID No. 1766436, Apr. 2012, www.gnpd.com.

* cited by examiner

*Primary Examiner* — Sue X Liu
*Assistant Examiner* — Ali S Saeed
(74) *Attorney, Agent, or Firm* — McNees Wallace & Nurick LLC

(57) ABSTRACT

The makeup removal composition includes at least one branched or linear, liquid alkane with carbon chain length of C11 to C20, at least one polar emollient with molecular weight of 400 g/mol or less, at least one polymeric thickener for water-based system, and at least one surfactant in a water-based emulsion/suspension system comprising oil and water phases, the water phase including water present from about 70% to about 85% by weight of the composition. Articles include the composition infused in a water-insoluble substrate formed from synthetic materials or formed from natural biodegradable and sustainably sourced natural originated fiber, natural fiber, or regenerated or recycled natural fiber.

19 Claims, 1 Drawing Sheet

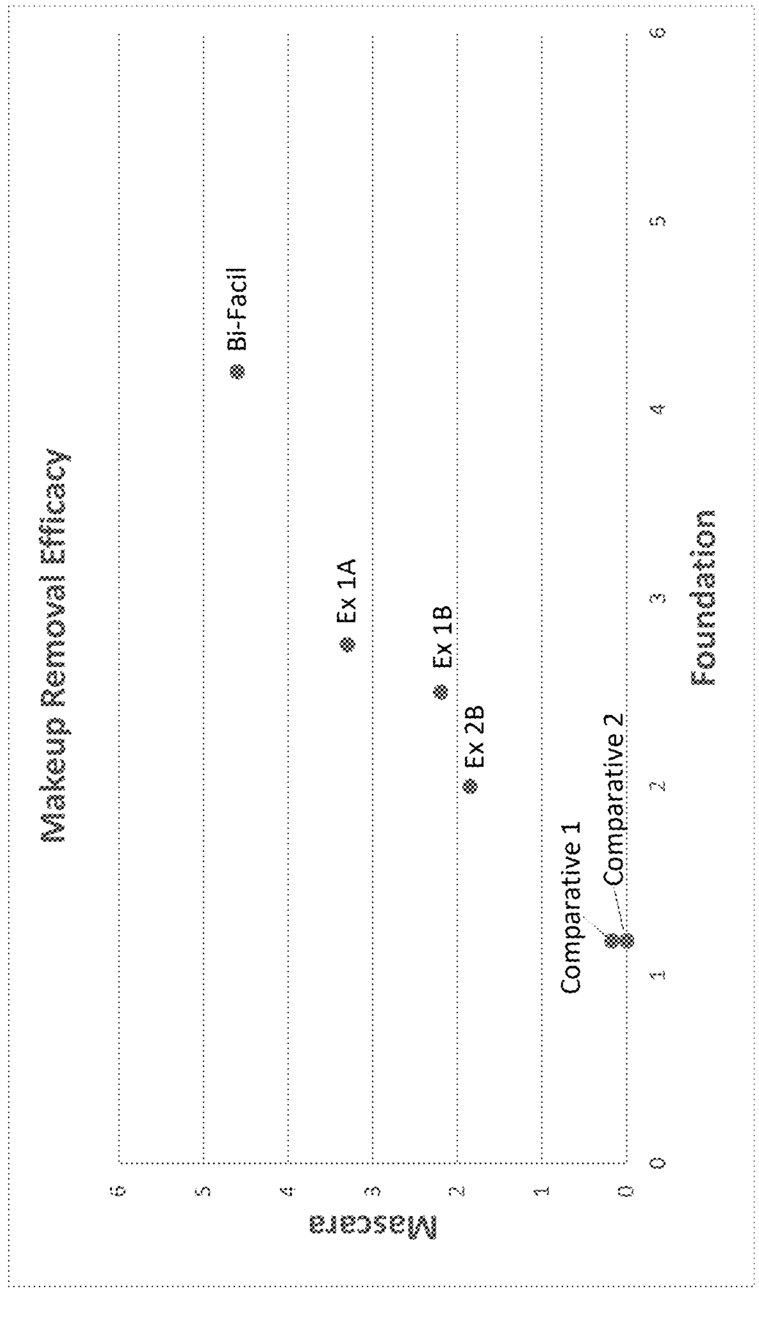
Makeup Removal Efficacy
Bi-Facil
Ex 1A
Ex 1B
Ex 2B
Comparative 1
Comparative 2
Mascara
Foundation
0
1
2
3
4
5
6

COMPOSITIONS AND ARTICLES FOR MAKE-UP REMOVAL

FIELD

This invention relates to makeup removal and cleansing juice compositions impregnated onto an article, having at least one water-insoluble substrate, particularly a wipe.

BACKGROUND

Removal of stubborn makeup has always been a challenge and a consumer pain point, particularly for waterproof mascara, long-wear foundation and longer-lasting lip products. Typical makeup removal products are ineffective in removing stubborn makeup, thus requiring repeated tugging and rubbing on the skin and/or the delicate eye areas, causing irritation. Some oil-based makeup removing products may provide ease of makeup removal but leave behind an unpleasant and greasy skin feel. Accordingly, there is a need for compositions and cleansing wipe articles that will provide easy and efficacious makeup removal in addition to a clean and refreshing skin feel after the use.

SUMMARY

The disclosure provides, in various embodiments, a makeup removal composition, comprising:

i. at least one branched or linear, liquid alkane with carbon chain length of C11 to C20;
ii. at least one polar emollient with a molecular weight of 400 g/mol or less;
iii. at least one polymeric thickener for water-based system;
iv. at least one surfactant; and
v. water present from about 70% to about 85% by weight of the composition.

In accordance with the various embodiments, compositions according to the disclosure include at least one branched or linear, liquid alkane with carbon chain length of C11 to C20, at least one polar emollient with molecular weight of 400 g/mol or less, at least one polymeric thickener for water-based system, and at least one alkylated glycerol ester in a water-based emulsion/suspension system comprising oily and water phases, the water phase including water present from about 70% to about 85% by weight of the composition. In various embodiments, the compositions may include more than one of each of the components, and may further include one or more additives including humectants, preservatives, fragrances, actives, and pH adjusters, among other cosmetically acceptable additives.

In accordance with some embodiments:

i. each of the at least one branched or linear, liquid alkane with carbon chain length of C11 to C20, is present from about 5% to about 10% by weight of the composition;
ii. each of the at least one polar emollient with a molecular weight of 400 g/mol or less is present from about 5% to about 10% by weight of the composition;
iii. each of the at least one polymeric thickener for water-based system is present from about 0.01% to about 2% by weight of the composition; and
iv. each of the at least one surfactant comprising alkylated glycerol ester is present up to about 2% by weight of the composition.

In some embodiments, the total amount of the one or more each alkylated glycerol ester does not exceed a total of about 2% by weight of the composition.

In accordance with some embodiments:

i. the at least one branched or linear, liquid alkane with carbon chain length of C11 to C20, comprises isohexadecane;
ii. the at least one polar emollient with molecular weight of 400 g/mol or less comprises isopropyl myristate;
iii. the at least one polymeric thickener for water-based system comprises carbomer; and
iv. the at least one surfactant comprising alkylated glycerol ester comprises PEG-7 glyceryl cocoate.

In accordance with some embodiments:

i. the branched or linear, liquid alkane with carbon chain length of C11 to C20 is selected from isohexadecane, C15-19 alkane, isododecane, undecane, tridecane and combinations thereof;
ii. the at least one polar emollient with molecular weight of 400 g/mol or less is selected from Isopropyl myristate, dicaprylyl ether, ethylhexyl palmitate, Isopropyl palmitate, cetearyl ethylhexanoate, Isononyl isononanoate, isopropyl isostearate, diisopropyl sebacate, coco caprylate/caprate, diisopropyl adipate, and combinations thereof;
iii. the at least one polymeric thickener is selected from carbomer, acrylates/C10-30 alkyl acrylate crosspolymer, polyacrylate crosspolymer-6, microcrystalline cellulose (and) cellulose gum, xanthan gum, sodium carboxymethyl starch, sclerotium gum (and) xanthan gum, xanthan gum (and) *Ceratonia siliqua* (carob) gum, dehydroxanthan gum, hydroxypropyl starch phosphate, sclerotium gum (and) xanthan gum, sclerotium gum, xanthan gum (and) sclerotium gum (and) lecithin (and) pullulan, and combinations thereof;
iv. the at least one surfactant is selected from PEG-7 glyceryl cocoate, PEG-7 caprylic/capric glycerides, PEG-6 caprylic/capric glycerides, disodium cocoyl glutamate (and) sodium cocoyl glutamate, coco-betaine, caprylyl/capryl glucoside, disodium cocoamphodiacetate, sodium cocoamphoacetate, polyglyceryl-4 caprate, and combinations thereof.

In some embodiments, the at least one polymeric thickener comprises carbomer and at least one or a combination of Acrylates/C10-30 Alkyl Acrylate Crosspolymer, Polyacrylate Crosspolymer-6, Microcrystalline Cellulose (and) Cellulose Gum, Xanthan Gum, Sodium Carboxymethyl Starch, Sclerotium Gum (and) Xanthan Gum.

In some embodiments, the composition includes one or a combination of additives selected from at least one humectant comprising glycerin, and at least one preservative comprising one or a combination of hydroxyacetophenone and caprylyl glycol.

In some embodiments, the composition is essentially free of silicone.

In some embodiments, a makeup removal and cleansing article is provided comprising:

a. A water-insoluble substrate comprising a cosmetic wipe;
b. Impregnated in the water-insoluble substrate a cleansing composition comprising;
   i. at least one branched or linear, liquid alkane with carbon chain length of C11 to C20, each present from about 5% to about 10% by weight of the composition, at least one branched or linear, liquid alkane comprising isohexadecane;
   ii. at least one polar emollient with molecular weight of 400 g/mol or less, each present from about 5% to about 10% by weight of the composition, the at least one polar emollient comprising isopropyl myristate;

iii. at least one polymeric thickener for water-based system, each present from about 0.01% to about 2% by weight of the composition, the at least one polymeric thickener comprising carbomer; and iv. a total amount of at least one surfactant comprising alkylated glycerol ester present up to about 2% by weight of the composition, the alkylated glycerol ester comprising PEG-7 glyceryl cocoate.

wherein the cleansing composition is impregnated onto the water-insoluble substrate in a soaking rate of 250% to 400% by weight of the cleansing composition to the weight of the substrate.

In accordance with the various embodiments, the makeup removal and cleansing article is formed from synthetic materials or formed from natural biodegradable and sustainably sourced natural originated fiber, natural fiber, or regenerated or recycled natural fiber.

In some particular embodiments, the makeup removal and cleansing article comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations of these.

These and other aspects of the invention are set out in the appended claims, and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

BRIEF DESCRIPTION OF THE DRAWING

Features and advantages of the general inventive concepts will become apparent from the following detailed description made with reference to the accompanying drawing.

The FIGURE is a data plot in the form of a 2D graph that shows the makeup removal efficacy of inventive compositions according to the disclosure and comparative compositions.

DETAILED DESCRIPTION

The term "article" is understood here to mean the combination composed of a water-insoluble support and a composition impregnated on the support. This article can in particular be a wipe but it can also have any form including those described below. The water-insoluble substrate is absorbent and sufficiently strong not to disintegrate during the use thereof. The use of the article as defined above for caring for the skin or hair and/or cleaning and/or removing makeup from and/or scrubbing the skin.

In some embodiments, the article may be formed of synthetic materials, such as PET (Polyethylene terephthalate, or polyester) and PP (polypropylene), which may be used alone or in combination with natural-based material. And in some embodiments, the article may be formed of sustainable and biodegradable substrates from sources such as (1) natural originated fiber based nonwovens, such as pulp, viscose, lyocell, cellulose acetate, cotton, (2) natural fiber based nonwovens, such as hemp, flax, seaweed, ramie, banana, pineapple, and (3) regenerated or recycled fiber based nonwovens, such as cotton.

Many conventional cosmetic articles, such as wipes, are formed of fossil-based polymeric materials, such as PET (Polyethylene terephthalate, or polyester) and PP (polypropylene), which may be used alone or in combination with natural-based material. Such synthetic substrates are desirable because they are relatively less costly to produce and deliver good tensile strength, however, because they essentially never degrade, they contribute adversely to the environment. With increasing focus in the cosmetics industry on sustainability, there is a need for cosmetic articles that employ solid substrates to draw from sources such as (1) natural originated fiber based nonwovens, such as pulp, viscose, lyocell, cellulose acetate, cotton, (2) natural fiber based nonwovens, such as hemp, flax, seaweed, ramie, banana, pineapple, and (3) regenerated or recycled fiber based nonwovens, such as cotton. As used herein, the terms "natural originated fiber" refers to fiber materials that are formed by chemical processing that render derivatives based on natural fibers; "natural fiber" means non-derivative forms of natural fibers, and "regenerated/recycled" means natural fibers that are reclaimed from goods formed with such fibers.

In some embodiments, the article herein is formed of substrates that are obtained from sustainable sources and are biodegradable. In some particular embodiments, these materials are selected from natural originated fiber formed into nonwovens, using fibers such as pulp, viscose, lyocell, cellulose acetate, and cotton. And in certain embodiments, the substrates used to form cosmetic articles are nonwovens of lyocell. According to those embodiments that include natural biodegradable and sustainably sourced fibers, a clear benefit realized is the opportunity to reduce the environmental burden. Other benefits may also be achieved using sustainable and biodegradable substrates. As further described herein, exemplified articles that employ sustainable and biodegradable substrates, particularly lyocell nonwovens, demonstrate unexpected mechanical, textural, and absorbent properties and significantly enhanced performance as compared with competitive cosmetic articles that employ synthetic materials. Also as described herein, exemplified articles that employ sustainable and biodegradable substrates, particularly lyocell nonwovens, demonstrate enhanced performance even as compared with inventive compositions hereof that are imbued in a synthetic substrate.

An article according to the disclosure is moist to the touch. It exhibits the advantage of being comfortable during application to the skin and having a nourishing effect due to the presence of an oily phase. When it is used for cleaning or removing makeup from the skin, an article according to the disclosure is passed over the skin, while possibly leaving it applied for a time sufficient for the makeup products to be dissolved in the impregnating composition of the article, and then the skin is wiped. The skin can also optionally be rinsed subsequently. The article according to the invention is preferably a cosmetic article appropriate for caring for and/or treating the skin of the face, body or hands and for cleaning or removing makeup from the skin of the face and/or body. It can also be used for caring for the hair and for removing makeup from the eyes.

An article according to the disclosure can have any form appropriate to the desired objective. It can constitute a wipe that has a generally rectangular, square or other shape that may be single ply, multiple ply, and may be folded or un-folded. The article can also be in the form of a glove, of a mitten or in any other form appropriate for practical use on the face or the body, for example in the form of a face with holes for the sites of the eyes, nose and/or mouth, or in the form of a makeup-removing fingerstall for application in removing makeup from the eyelashes, or in the form of a single- or double-sided disc which can in particular comprise two sides impregnated with different compositions. The article can also comprise a rough surface which makes possible the exfoliation (scrubbing) of the skin.

"Keratinous substrate" and "keratinous tissue" each includes but is not limited to skin, hair, and nails.

"Cosmetically acceptable" means a carrier that is compatible with any keratinous substrate.

The term "silicone-free" as used herein means containing less than 5%, such as less than 3%, such as less than 1% by weight, based on the total active weight of the composition, of silicones, such as silicone polymers, for example selected from dimethicone and other silicone oils, and silicon elastomers.

According to the disclosure, the inventive compositions overcome the shortcomings of the prior art and provide unexpected benefits that include ease with overall makeup removal, easy foundation removal, leaves skin feeling clean and fresh, soft and smooth, easy mascara removal (regular and waterproof) with no rubbing, satisfying size and thickness of substrate (wipe), not too dry, non-greasy, does not leave a residue and pleasant fragrance.

Through expert evaluations of makeup removal efficacy, compositions according to the disclosure demonstrated significantly better performance in removing waterproof mascara and long-wear foundation as compared with currently marketed makeup removal wipes, for example Neutrogena™ Makeup Remover Cleansing Towelettes and Garnier™ SkinActive Clean+ Refreshing Remover Cleansing Towelettes, both formed with synthetic fiber substrates imbued with cleansing compositions.

In a consumer study, inventive compositions according to the disclosure not only performed better in makeup removal efficacy, including improved performance in the removal of both foundation and mascara, but also provided an experience for consumer testers that was more pleasing and resulted in comparatively better skin feel after use. Inventive articles formed using natural fiber demonstrated similar enhanced performance versus comparative compositions and also versus the same inventive compositions imbued in synthetic fiber substrate. The compositions according to the disclosure have a clean and fresh feel when applied, and do not leave skin feeling greasy or sticky.

Compositions according to the disclosure include at least one branched or linear, liquid alkane with carbon chain length of C11 to C20, at least one polar emollient with molecular weight of 400 g/mol or less, at least one polymeric thickener for water-based system, and at least one alkylated glycerol ester in a water-based emulsion/suspension system comprising oily and water phases, the water phase including water present from about 70% to about 85% by weight of the composition. In various embodiments, the compositions may include more than one of each of the components, and may further include one or more additives including humectants, preservatives, fragrances, actives, and pH adjusters, among other cosmetically acceptable additives.

(I) Branched or Linear, Liquid Alkane

In accordance with the disclosure, the compositions include at least one branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some particular embodiments, suitable liquid alkanes that may be used according to the disclosure include hydrocarbon-based oils containing from 8 to 16 carbon atoms, and especially branched C8-C16 alkanes such as C8-C16 isoalkanes. In some exemplary embodiments, such liquid alkanes may be chosen from isoparaffins, for instance isododecane (also known as 2,2,4,4,6-pentamethylheptane), isodecane, and isohexadecane.

In some embodiments, the least one branched or linear, liquid alkane comprises isohexadecane, C15-19 alkane, isododecane, undecane, tridecane and combinations thereof. In some embodiments the composition comprises two or more branched or linear, liquid alkanes. In some such embodiments, the branched or linear, liquid alkane comprises isohexadecane.

The amount of each of the at least one branched or linear, liquid alkane is present in the composition in a range of from about 1% to about 12% by weight, or from about 3% to about 11% by weight, or from about 5% to about 10% or any suitable combination, sub-combination, range, or sub-range thereof by weight, based on the weight of the composition. One of ordinary skill in the art, however, will appreciate that other ranges are within the scope of the invention.

Thus, each of the at least one branched or linear, liquid alkane in the composition may be present by weight, based on the total weight of the composition, from about 1, 2, 3, 4, 5, 6, 7, 8, 9, to about 10 percent, including increments and ranges therein and there between.

(ii) Polar Emollients

In accordance with the disclosure, the compositions include at least one polar emollient. Emollients are oil-phase ingredients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol to about 350 g/mol.

In some embodiments, suitable polar emollients that may be used according to the disclosure include those derived from C12-C50 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

In some embodiments, the one or more polar emollient comprises one of isopropyl myristate, dicaprylyl ether, ethylhexyl palmitate, isopropyl palmitate, cetearyl ethylhexanoate, isononyl isononanoate, isopropyl isostearate, diisopropyl sebacate, coco caprylate/caprate, diisopropyl adipate, and combinations thereof. In some particular embodiments the one or more polar emollient includes isopropyl myristate. In some embodiments the composition comprises two or more polar emollients. In some such embodiments, the polar emollient comprises isopropyl myristate and one or more additional polar emollients.

The amount of each of the at least one polar emollient is present in the composition in an range of from about 1% to about 12% by weight, or from about 3% to about 11% by weight, or from about 5% to about 10% or any suitable combination, sub-combination, range, or sub-range thereof by weight, based on the weight of the composition. One of ordinary skill in the art, however, will appreciate that other ranges are within the scope of the invention.

Thus, each of the at least one polar emollient in the composition may be present by weight, based on the total weight of the composition, from about 1, 2, 3, 4, 5, 6, 7, 8, 9, to about 10 percent, including increments and ranges therein and there between.

(iii) Polymeric Thickener

In accordance with the various embodiments, the compositions include one or more polymeric thickeners. In some embodiments, the one or more thickener may be selected from one or more of natural gums and synthetic polymers, for example starches (corn, rice, tapioca, potato), gums (xanthan carrageenan, gellan, sclerotium, tarabiotech fermentation). In some particular embodiments, the thickener may be selected from acrylates/C10-30 alkyl acrylate crosspolymer, carbomer, xanthan gum, hydroxypropyl guar, *Ceratonia siliqua* (carob) gum, ammonium polyacryloyldimethyl taurate, ammonium acryloyldimethyltaurate/steareth-25 methacrylate crosspolymer, and polyacrylate crosspolymer-6.

In some embodiments, the polymeric thickener is one of carbomer, acrylates/C10-30 alkyl acrylate crosspolymer, polyacrylate crosspolymer-6, microcrystalline cellulose (and) cellulose gum, xanthan gum, sodium carboxymethyl starch, sclerotium gum (and) xanthan gum, xanthan gum (and) *Ceratonia siliqua* (carob) gum (50/50), dehydroxanthan gum, hydroxypropyl starch phosphate, sclerotium gum (and) xanthan gum (75/25), sclerotium gum, xanthan gum (and) sclerotium gum (and) Lecithin (and) pullulan, and combinations thereof.

In some embodiments the composition comprises two or more polymeric thickeners. In some such embodiments, the polymeric thickener comprises one or both of acrylates/C10-30 alkyl acrylate crosspolymer and carbomer, and optionally one or more additional polymeric thickeners.

The amount of each of the at least one polymeric thickener is present in the composition in a range of from about 0.01% to about 2%, or from about 0.01% to about 1.5%, or from about 0.3% to about 1.2%, or any suitable combination, sub-combination, range, or sub-range thereof by weight, based on the weight of the composition. One of ordinary skill in the art, however, will appreciate that other ranges are within the scope of the invention.

In some embodiments, the total amount of polymeric thickener in the composition is present from about 0.01% to about 5%, or from about 0.02% to about 2%, or from about 0.03% to about 1.5%, or from about 0.1% to about 0.2%, or any suitable combination, sub-combination, range, or sub-range thereof by weight, based on the weight of the composition. One of ordinary skill in the art, however, will appreciate that other ranges are within the scope of the invention.

Thus, one or more polymeric thickener is present by weight, based on the total weight of the composition, from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

(iv) Alkylated Glycerol Ester/Surfactant

In accordance with the various embodiments, the compositions include at least one alkylated glycerol ester/surfactant. In some embodiments, the one or more surfactant may be selected from esters of polyols with fatty acids with a saturated or unsaturated chain containing for example from 8 to 24 carbon atoms (e.g., 12 to 22 carbon atoms), and alkoxylated derivatives thereof, such as glyceryl esters of a C8-C24 fatty acid or acids and alkoxylated derivatives thereof, polyethylene glycol esters of a C8-C24 fatty acid or acids and alkoxylated derivatives thereof, sorbitol esters of a C8-C24 fatty acid or acids and alkoxylated derivatives thereof, sugar (sucrose, glucose, alkylglucose) esters of a C8-C24 fatty acid or acids and alkoxylated derivatives thereof, ethers of fatty alcohols, ethers of sugar and a C8-C24 fatty alcohol or alcohols, and mixtures thereof.

In some embodiments the composition comprises at least one, and in some embodiments, two or more alkylated glycerol esters. In some such embodiments, the alkylated glycerol ester comprises one or more of PEG-7 glyceryl cocoate, PEG-7 caprylic/capric glycerides, PEG-6 caprylic/capric glycerides, disodium cocoyl glutamate (and) sodium cocoyl glutamate, coco-Betaine, caprylyl/capryl glucoside, Disodium cocoamphodiacetate, sodium cocoamphoacetate, polyglyceryl-4 caprate, and combinations thereof.

In some embodiments, each of the at least one alkylated glycerol ester in the composition is present from about 0.1% to about 2%, or from about 0.2% to about 1.5%, or from about 0.5% to about 1%, or any suitable combination, sub-combination, range, or sub-range thereof by weight, based on the weight of the composition. One of ordinary skill in the art, however, will appreciate that other ranges are within the scope of the invention.

In some particular embodiments, the total amount of alkylated glycerol ester/surfactant is present up to about 2%. In some embodiments the total amount of alkylated glycerol ester/surfactant does not exceed about 2%. In some particular embodiments, the total amount of alkylated glycerol ester/surfactant is less than about 2%.

Thus, each of the at least one alkylated glycerol ester is present by weight, based on the total weight of the composition, from about 0.1, 0.2, 0.3, 0.4, 0.5, 0.55, 0.6, 0.7, 0.75, 0.8, 0.9, 1.0, 1.1, 1.2, 1.3, 1.4, 1.5, 1.6, 1.7, 1.8, 1.9, to about 2.0 percent, including increments and ranges therein and there between.

(v) Solvent/Water

In accordance with the various embodiments, water is present in the compositions in a range from about 60% to about 90%, or from about 65% to about 85%, or from about 70% to about 85%, or from about 75% to about 80%, or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 60, 65, 70, 75, 80, 85, to about 90 weight percent, including increments and ranges therein and there between The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition is not limited but is generally between 2 and 12, and in some embodiments, is one of between 3 and 11, and between 5 and 9, and between 6 and 8, and in some embodiments is 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

In some embodiments, the composition can include one or more additional solvents, for example, monoalcohols such as monohydric $C_1$-$C_8$ alcohols such as ethanol, propanol, butanol, isopropanol, isobutanol, and benzyl alcohol, and phenylethyl alcohol.

Humectant/Hydrating Agent

In accordance with the disclosure, one more humectants may be present in the compositions. In some embodiments, the humectant may comprise one or more of polyols, including, for example, glycerin, glycerol, glycols, such as caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl(C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the compositions include a humectant comprising glycerin.

In accordance with the various embodiments, the amount of humectant present in the compositions can range from about 1% to about 10%, or from about 1% to about 8%, or from about 1% to about 5%, or from about 2% to about 3%, or any suitable combination, sub-combination, range, or sub-range thereof by weight, based on the weight of the composition. One of ordinary skill in the art, however, will appreciate that other ranges are within the scope of the invention.

Thus, any one of or a combination of humectant may be present, by weight, based on the total weight of the composition, is from about 1, 2, 3, 4, 5, 6, 7, 8, 9, to about 10 weight percent, including increments and ranges therein and there between.

Optional Additives

The compositions can also comprise at least one additive used in the cosmetics field which does not affect the properties of the compositions according to the invention, such as fragrances, pearlescent agents, silica, preservatives, proteins, protein hydrolysates, vitamins, panthenol, silicones, odor absorbers and coloring materials; anti-microbial components, including, but not limited to, capryloyl glycine and sodium salicylate; essential oils; fruit extracts, for example *Pyrus Malus* (Apple) Fruit Extract, and Aloe Barbadensis Leaf Juice Powder; citric acid, sodium chloride; neutralizing or pH-adjusting agents (e.g., triethylamine (TEA) and sodium hydroxide), preservatives, and combinations thereof. In some embodiments, the compositions include at least one preservative comprising one or a combination of hydroxyacetophenone and caprylyl glycol.

Although the optional active additives are given as examples, it will be appreciated that other optional components compatible with cosmetic applications known in the art may be used. Although the optional additives are given as examples, it will be appreciated that other optional components compatible with cosmetic applications known in the art may be used.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Substrate

In accordance with the various embodiments, provided are articles comprising a solid substrate imbued with an inventive makeup removal composition. The makeup removal and cleansing article is formed from synthetic materials or formed from natural biodegradable and sustainably sourced natural originated fiber, natural fiber, or regenerated or recycled natural fiber.

According to some embodiments, the substrate is a nonwoven material. A general description of nonwoven materials is given in Riedel "Nonwoven Bonding Methods and Materials", Nonwoven World (1987). These substrates are obtained according to the normal methods of the technology for the preparation of nonwoven materials.

When the substrate is a nonwoven material, use may be made of a nonwoven material which does not go into ball and which is sturdy enough not to disintegrate and not to become fluffy when applied to the skin. It must be absorbent and soft at least on one side for the removal of makeup from the eyes in particular. Mention may be made, as appropriate nonwoven materials, for example, of those sold under the names Ultraloft 15285-01, Ultraloft 182-008, Ultraloft 182-010 and Ultraloft 182-016 by BBA, Vilmed M1519 Blau, Vilmed M 1550 N and 112-132-3 by Freudenberg, that sold under the name Norafin 11601-010B by Jacob Holm Industries, the flocked nonwoven materials sold under the names Univel 109 and Univel 119 by Uni Flockage and that made of viscose/PLA supplied by Sandier.

According to some embodiments comprising an article, a water insoluble substrate is employed. The water-insoluble substrate can comprise one or more layers and it can be chosen from the group consisting of woven materials, nonwoven materials, foams, sponges, waddings, as sheets, balls or films. It can in particular be a nonwoven substrate based on fibers of natural origin (flax, wool, cotton, silk, viscose, fibers made of bamboo) or synthetic origin (cellulose derivatives, polyvinyl derivatives, polyesters, such as poly(ethylene terephthalate), polyolefins, such as polyethylene (PET) or polypropylene, polyamides, such as Nylon, or acrylic derivatives) and their mixtures, such as viscose/PET, polylactic acid (PLA) or viscose/polylactic acid (viscose/PLA).

According to one embodiment, the substrate is a nonwoven material, composed of viscose or a nonwoven material composed of a viscose/microviscose mixture, through a hydro entanglement process.

In some particular embodiments, the makeup removal and cleansing article comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations of these.

According to one embodiment, the substrate is a nonwoven material formed of a biodegradable material, such as lyocell.

According to some embodiments, the substrate can comprise one or more layers having identical or different properties and having properties of elasticity and of softness and other properties appropriate to the desired use. The substrates can comprise, for example, two parts having different elasticity properties, as described in the document WO-A-99/13861, or can comprise a single layer having different densities, as described in the document WO-A-99/25318, or can comprise two layers of different textures, as described in the document WO-A-98/18441.

According to some embodiments, when the article is used for the body, the substrate can comprise at least one rough side for making it possible, at the same time, to massage the skin or to scrub the skin.

According to the various embodiments, the substrate can have any size and any shape which are appropriate for the desired objective. Furthermore, it generally has a surface area of between 0.005 $m^2$ and 0.1 $m^2$, or from between 0.01 $m^2$ and 0.05 $m^2$. The weight of the substrate can be in a range between 30 gsm to 200 gsm (gram per square meter), or from between 40 gsm to 60 gsm.

According to the various embodiments, the degree of impregnation of the composition onto the substrate generally ranges from 100 to 1000%, in some embodiments from about 150% to about 700%, or from about 250% to about 400% of the weight of the substrate. The techniques for impregnating the substrates with compositions are well known and can all be applied in the present invention. Generally, the impregnating composition is heated and added to the substrate by one or more techniques comprising immersion, coating, spraying, and the like.

The examples below according to the invention are given by way of illustration and without a limiting nature. The names are the chemical name or the INCI name. The amounts are given therein as % by weight, unless otherwise mentioned.

EXAMPLES

Example 1: Raw Materials

TABLE 1

| Raw Materials | | |
|---|---|---|
| Phase | INCI Name | Notes and Commercial Sources |
| A | Water | |
| A | Carbomer | Carbopol Ultrez ™ 10 Polymer |
| A | Aerylates/C10-30 Alkyl Acrylate Crosspolymer | Pemulen ™ TR-2 |
| A | Polyacrylate Crosspolymer-6 | Seppic - Sepimaz Zen ™ |
| A | Microcrystalline Cellulose (and) Cellulose Gum | FMC ™-Avicel PC 611 |
| A | Xanthan Gum | Multiple sources |
| A | Sodium Carboxymethyl Starch | Roquette ™ - Glycolys (Com Starch) |
| A | Sclerotium Gum (and) Xanthan Gum | Cargill ™ - Actigum VSX 20 |
| A | Xanthan Gum (and) *Ceratonia Siliqua* (Carob) Gum | Nisshin Oil Lio - Nomcort CG ™ |
| A | Dehydroxanthan Gum | Akzo Nobel ™ - Amaze XL |
| A | Hydropropyl Starch Phosphate | Akzo Nobel ™ - Structure XL |
| A | Sclerotium Gum (and) Xanthan Gum | Cargill ™ - Actigum VSX 20 |
| A | Sclerotium Gum | Alban Muller ™ - Amigum |
| A | Xanthan Gum (and) SCLEROTIUM GUM (and) LECITHIN (and) PULLULAN | Lucas Meyer ™ - Siligel |
| B | Water | |
| B | Glycerin | Humectant |
| B | Caprylyl Glycol | Preservative |
| B | Hydroxyacetophenone | Preservative, Symrise - SymSave H ™, |
| C | Sodium Hydroxide | pH Adjuster (50% In Water) |
| D | Isododecane | Alkanes |
| D | Isohexadecane | Alkanes |
| D | C15-19 Alkane | Alkanes |
| D | Undecane (and) tridecane | Alkanes |
| D | Isopropyl Myristate | emollient ester |
| D | Dicaprylyl Ether | emollient ether |
| E | PEG-7 Glyceryl Cocoate | BASF ™ - Cetiol HE |
| E | PEG-7 Caprylic/Capric Glycerides | BASF ™ - Cetiol |

TABLE 1-continued

| Raw Materials | | |
|---|---|---|
| Phase | INCI Name | Notes and Commercial Sources |
| E | PEG-6 Caprylic/Capric Glycerides | Cremer Oleo ™- Softigen 767 |
| E | Disodium Cocoyl Glutamate (and) Sodium Cocoyl Glutamate | Ajinomoto ™-Amisoft CS22 |
| E | Coco-Betaine | Multiple sources |
| E | Caprylyl/Capryl Glucoside | Seppic ™ - Oramix CG110 |
| E | Disodium Cocoamphodiacetate | Rhodia ™ - Miranol |
| E | Sodium Cocoamphoacetate | Rhodia ™ - Miranol Ultra C32 |
| E | Polyglyceryl-4 Caprate | Evonik ™ - Tegosoft PC41 |
| F | Fragrance | |

Example 2: Inventive Compositions

Various representative embodiments of the inventive compositions and articles are exemplified herein. In some instances, the composition is referred to as a "juice." Inventive compositions in juice form (not imbued in a substrate) are designated with a numeric identifier (e.g., "Inventive Composition 1" or "INV 1"); inventive compositions in article form (imbued in a substrate) are designated with an alphanumeric identifier (e.g., "Inventive Composition 1A" or "INV 1A" (juice imbued in a biodegradable lyocell nonwoven); "Inventive Composition 1B" or "INV 1B" (juice imbued in a synthetic nonwoven substrate)).

TABLE 2

| Inventive Compositions | | | | | | | | | |
|---|---|---|---|---|---|---|---|---|---|
| Phase | INCI Name | INV Ex 1 | INV Ex 2 | INV Ex 3 | INV Ex 4 | INV Ex 5 | INV Ex 6 | INV Ex 7 | INV Ex 8 |
| A | Water (QS) | 58.47 | 58.47 | 58.47 | 58.37 | 59.5 | 57.39 | 58.3 | 56.47 |
| A | Carbomer | 0.1 | 0.1 | 0.1 | 0.1 | | | | 0.1 |
| A | Acrylates/C10-30 Alkyl Acrylate Crosspolymer | 0.03 | 0.03 | 0.03 | 0.03 | | | | 0.03 |
| A | Polyacrylate Crosspolymer-6 | | | | | 0.15 | | | |
| A | Microcrystalline Cellulose (and) Cellulose Gum | | | | | | 1.2 | | |
| A | Xanthan Gum | | | | | | 0.01 | | |
| A | Sodium Carboxy-methyl Starch | | | | | | | 0.1 | |
| A | Sclerotium Gum (and) Xanthan Gum | | | | | | | 0.2 | |
| B | Water | 25 | 25 | 25 | 25 | 25 | 25 | 25 | 25 |
| B | Glycerin | 3 | 3 | 3 | 3 | 3 | 3 | 3 | 3 |
| B | Caprylyl Glycol | 0.3 | 0.3 | 0.3 | 0.3 | 0.3 | 0.3 | 0.3 | 0.3 |
| B | Hydroxyaceto-phenone | 0.5 | 0.5 | 0.5 | 0.5 | 0.5 | 0.5 | 0.5 | 0.5 |
| C | Sodium Hydroxide | 0.05 | 0.05 | 0.05 | 0.05 | 0.05 | 0.05 | 0.05 | 0.05 |
| C | Water | 0.5 | 0.5 | 0.5 | 0.5 | 0.5 | 0.5 | 0.5 | 0.5 |
| D | Isohexadecane | 5 | | 5 | 5 | 5 | 5 | 5 | 5 |
| D | C15-19 Alkane | | 5 | | | | | | |
| D | Isopropyl Myristate | 5 | 5 | 5 | 5 | 5 | 5 | 5 | 5 |
| D | Dicaprylyl Ether | 1 | 1 | 1 | 1 | 1 | 1 | 1 | 1 |
| E | PEG-7 Glyceryl Cocoate | 1 | 1 | | | | | | |
| E | PEG-7 Caprylic/ Capric Glycerides | | | 1 | | | | | 1 |
| E | PEG-6 Caprylic/ Capric Glycerides | | | | | | 1 | | |
| E | Disodium Cocoyl Glutamate (and) Sodium Cocoyl Glutamate (20.2/4.8) | | | | 0.5 | | | | |
| E | Coco-Betaine (30%, 6.5% NaCl In Water) | | | | 0.4 | | | | 1 |
| E | Caprylyl/Capryl Glucoside | | | | 0.2 | | | | |
| E | Disodium Cocoamp-hodiacetate | | | | | | | 0.5 | |
| E | Sodium Coco-amphoacetate | | | | | | | 0.5 | |
| E | Polyglyceryl-4 Caprate | | | | | | | | 1 |

TABLE 2-continued

| Phase | INCI Name | INV Ex 1 | INV Ex 2 | INV Ex 3 | INV Ex 4 | INV Ex 5 | INV Ex 6 | INV Ex 7 | INV Ex 8 |
|---|---|---|---|---|---|---|---|---|---|
| | Inventive Compositions | | | | | | | | |
| F | Fragrance | 0.05 | 0.05 | 0.05 | 0.05 | 0.05 | 0.05 | 0.05 | 0.05 |
| | Total (%): | 100 | 100 | 100 | 100 | 100 | 100 | 100 | 100 |
| | Appearance | White Lotion | | | | | | | |
| | pH | 6.8-7.1 | | | | | | | |
| | Viscosity* (Cp) | 400-1200 | | | | | | | |

*Brookfield RVT Viscometer, Helipath Spindle T-A, 10 Rpm, 1 min

Example 3: Inventive Preparation Procedures

Preparation of juice formulas: 1. Prepare phase A by slowly adding polymeric thickeners to water at room temperature and mix well using an overhead propeller mixer with a Cowles blade (500-800 rpm for 20-30 min) until homogeneous and have no lumps or gel bodies. 2. Prepare phase B (water phase) by mixing B ingredients using a stirring bar and heat to 55-60 degrees C., until all solids are dissolved, giving a hazy, but homogeneous, colorless liquid. Stop heating. 3. Add B to A and mix well. 4. Prepare pH adjuster by mixing sodium hydroxide in water (Phase C) and add to AB. Mix well. 5. Add D (oil phase), E (surfactants) and F (fragrance) to ABC (800 rpm) one ingredient at a time, or premix in a beaker. 6. Mix well at room temperature and drop the batch. Take specifications (pH, viscosity).

Preparation of makeup removing wipes: Homogeneously soak the chosen nonwoven substrate with a juice formulation in a weight percent ratio of 1:4 (substrate: juice formula) manner. Fold the wet substrates into a desired shape, stack the folded wet wipes and pack into a suitable package for ease of use.

TABLE 3

| Inventive Wipes | Juice Composition | Substrate Composition | Juice:Substrate (wt) |
|---|---|---|---|
| Inventive Wipe Compositions | | | |
| Ex 1A | INV Ex. 1 | 100% lyocell | 4:1 |
| Ex 1B | INV Ex. 1 | 50% PET, 32% viscose, 18% PP | 4:1 |
| Ex 2B | INV Ex. 2 | 50% PET, 32% viscose, 18% PP | 4:1 |

Example 4: Comparative Compositions

TABLE 4

| Ingredients | Weight (g) |
|---|---|
| Comparative Composition 1 - NEUTROGENA ™ Makeup Remover Cleansing Towelettes (weight composition is based on Example 18 from U.S. Pat. No. 7,262,158 and chromatographic analysis results) | |
| Water (QS) | 866.663 |
| Cetyl Ethylhexanoate | 20 |
| Isostearyl Palmitate | 20 |
| Pentaerythrityl Tetraethylhexanoate | 20 |
| Isononyl Isononanoate | 20 |
| Cyclopentasiloxane | 20 |
| Hexylene Glycol | 10 |
| PEG-6 Caprylic/Capric Glycerides | 7.5 |

TABLE 4-continued

| Ingredients | Weight (g) |
|---|---|
| Comparative Composition 1 - NEUTROGENA ™ Makeup Remover Cleansing Towelettes (weight composition is based on Example 18 from U.S. Pat. No. 7,262,158 and chromatographic analysis results) | |
| PEG-4 Laurate (and) Sucrose Cocoate | 10 |
| Carbomer | 5 |
| Sodium Hydroxide | QS to pH 5.5 |
| Benzoic Acid | 0.47 |
| Dehydroacetic Acid | 0.069 |
| Phenoxyethanol | 6.5 |
| Iodopropynyl Butylcarbamate | 0.29 |
| Fragrance (EU 1279) | 0.5 |
| Total Wt (g) | 1000 |

TABLE 5

| Ingredients | Weight Percent* |
|---|---|
| Comparative Composition 2 - GARNIER ™ Clean + Refreshing Towelettes | |
| Aqua/Water | |
| Isohexadecane* | 1.99 |
| Dicaprylyl Ether* | 1.98 |
| *Vitis Vinifera* Fruit Water/Grape Fruit Water | |
| Hexylene Glycol | |
| Phenoxyethanol | |
| Sorbitan Laurate | |
| Acrylates/C10-30 Alkyl Acrylate Crosspolymer | |
| Tetrasodium Glutamate Diacetate | |
| Propylene Glycol | |
| Aminomethyl Propanol | |
| Parfum/Fragrance | |
| Lauryl Glucoside | |
| Polyglyceryl-2 Dipolyhydroxystearate | |
| Glycerin | |
| Citric Acid | |
| Iodopropynyl Butylcarbamate | |
| Linalool | |
| Benzyl Salicylate | |
| Limonene | |
| Pentylene Glycol | |
| *Mentha Piperita* Extract/Peppermint Extract | |
| Benzyl Alcohol | |
| Tocopherol | |
| Tocopheryl Acetate | |

*Weight percentage is based on chromatographic analysis results.

Example 5: Expert Evaluation: Demonstration of the Effectiveness of Inventive Compositions Vs Comparative Compositions in Stubborn Makeup and Mascara Removal A study was conducted to evaluate the effectiveness of the inventive compositions in comparison with commercially available makeup removing wet wipes (comparative compositions), having generally similar components infused in a solid substrate. In the study, wipe substrates impregnated with juice compositions were used by trained/expert aesthetician to remove heavy face makeup (Maybelline™ Super Stay Full Coverage Foundation), and mascara (Maybelline™ Colossal Big Shot Waterproof Mascara). The cleansing wipes were prepared by soaking the liquid cleaning composition with a wipe substrate in a specific weight percentage ratio, typically 4:1 (juice: substrate). The makeup removal efficacy was determined by following a protocol under which the aesthetician applied stubborn makeup products on six (6) Caucasian women. After 30 min, the aesthetician removed the makeup with test products (inventive and comparative) and the degree of removal was assessed by the amount of residual makeup that was removed by using Lancôme™ Bi-Facil™ Makeup Remover (a two-phase make-up removal product), 2 mL on a cotton pad for up to 6 cotton pads. The higher the makeup removal efficacy of the test formula would require fewer cotton pads with Bi-Facil™ to remove, as there would be less residual makeup. The makeup removal efficacy data was plotted using a 2D graph, shown as the FIGURE; the data as shown in the FIGURE are represented in Table 6.

TABLE 6

Make-Up Removal Efficacy (scale of 1 to 6:6 being complete removal, and 1 being no removal)

| Test Composition | Foundation | Mascara |
|---|---|---|
| Neutrogena ™ (Comparative 1) | 1.18 | 0.18 |
| Garnier ™ (Comparative 2) | 1.18 | 0.18 |
| Inventive Ex 1A | 2.5 | 2.2 |
| Inventive Ex 1B | 2.75 | 3.3 |
| Inventive Ex 2B | 2.0 | 1.85 |
| Bi-Facil (Two-phase product) | 4.2 | 4.6 |

Both tested inventive compositions are more efficient in foundation and mascara removal as compared with each of the comparative compositions, and both inventive compositions provided aesthetically acceptable results.

Example 6: Demonstration of the Effectiveness of Inventive Compositions Vs Comparative Composition 1 (Neutrogena™) in Removal of Consumer Selected Makeup and Mascara; in-Home User Evaluation Studies were conducted to evaluate the effectiveness of representative inventive compositions provided as infused wipe articles in comparison with comparative composition commercially available as makeup removing wipes (Comparative 1).

Consumers who met the following criteria signed up to participate in the trial:

Females age 18-55; Wear foundation (stubborn or regular) and mascara (waterproof or regular) for more than 3 days per week; Use Neutrogena™ Ultra Soft makeup removal wipes (blue pack) at least once per week.

Example 6A: Demonstration of the Effectiveness of Inventive Compositions Vs Comparative Composition 1 (Neutrogena™) in Removal of Consumer Selected Makeup and Mascara; in-Home User Evaluation Three groups of participants (60 women in each group) used the test product, selected from Inventive Ex 1B, Inventive Ex 2B, or Comparative 1, over one-week period, and after one-week of usage, participated in an online survey. Results showing the generally comparable or superior performance of the inventive compositions are shown in Table 7.

TABLE 7

Results from compiled consumer testing performance of two Inventive compositions vs Comparative Example 1 - NEUTROGENA ™ Makeup Remover Cleansing Towelettes

| Performance: Removal | Comparative Composition 1 SYNTHETIC NONWOVEN SUBSTRATE | Inventive Composition 1B SYNTHETIC NONWOVEN SUBSTRATE | Inventive Composition 2B SYNTHETIC NONWOVEN SUBSTRATE |
|---|---|---|---|
| Face Make-up | YES | YES | YES |
| Eyeliner | PART | YES | YES |
| Eye Shadow | YES | YES | YES |
| Overall Mascara (easily/well) | YES | YES | YES |
| Overall Mascara (w/o rubbing) | NO | PART | PART |
| Water-proof Mascara (easily/well) | YES | YES | YES |
| Water-proof Mascara (without rubbing) | PART | YES | NO |
| Lipstick | YES | YES | YES |

KEY:
YES = positive experience;
NO = negative experience;
PART = unsatisfactory

Example 6B: Demonstration of the Effectiveness of Inventive Composition on Different Substrates Vs Comparative Composition 1 (Neutrogena™) in Removal of Consumer Selected Makeup and Mascara; in-Home User Evaluation Three groups of participants used the test product, selected from Inventive Ex 1A (lyocell substrate)—62 participants/subjects, Inventive Ex 11B (PET/viscose/PP substrate)—61 participant subjects, or Comparative 1-54 participant subjects, over a period of three weeks, and after the first week of use, participated in an online survey. Results showing the generally comparable or superior performance of the inventive compositions are shown in Table 8. Surprisingly, Inventive Ex 1A (lyocell substrate) exhibited better makeup removing efficacy and better skin feel than Inventive Ex 11B (PET/Viscose/PP substrate), indicating a superior performance with lyocell substrate.

TABLE 8

Results from compiled consumer testing performance of two different substrates for Inventive Composition EX 1 vs Comparative Example 1 - NEUTROGENA ™ Makeup Remover Cleansing Towelettes

| Performance: Removal | Comparative Composition 1 SYNTHETIC NONWOVEN SUBSTRATE | Inventive Composition 1B SYNTHETIC NONWOVEN SUBSTRATE | Inventive Composition 1A LYOCELL SUBSTRATE |
|---|---|---|---|
| Face Make-up | YES | YES | YES |
| Eyeliner | YES | YES | YES |
| Eye Shadow | YES | YES | YES |

TABLE 8-continued

Results from compiled consumer testing performance of two different substrates for Inventive Composition EX 1 vs Comparative Example 1 - NEUTROGENA ™ Makeup Remover Cleansing Towelettes

| Performance: Removal | Comparative Composition 1 SYNTHETIC NONWOVEN SUBSTRATE | Inventive Composition 1B SYNTHETIC NONWOVEN SUBSTRATE | Inventive Composition 1A LYOCELL SUBSTRATE |
|---|---|---|---|
| Overall Mascara (easily/well) | YES | YES | YES |
| Overall Mascara (w/o rubbing) | PART | PART | YES |
| Water-proof Mascara (easily/well) | YES | YES | YES |
| Water-proof Mascara (without rubbing) | PART | PART | YES |
| Lipstick | YES | YES | YES |

KEY:
YES = positive experience;
NO = negative experience;
PART = unsatisfactory

TABLE 8

Results from compiled consumer testing performance of two different substrates for Inventive Composition EX 1 vs Comparative Example 1 - NEUTROGENA ™ Makeup Remover Cleansing Towelettes

| Performance: Skin Feel | Comparative Composition 1 NONWOVEN SYNTHETIC SUBSTRATE | Inventive Composition 1B NONWOVEN SYNTHETIC SUBSTRATE | Inventive Composition 1A NONWOVEN LYOCELL SUBSTRATE |
|---|---|---|---|
| Clean & Fresh | YES | PART | YES |
| Soft & Smooth | YES | PART | YES |
| Not Greasy | YES | YES | YES |
| Not Sticky | YES | YES | YES |
| Not Dry | YES | YES | YES |
| Does Not Leave Residue | YES | YES | YES |
| Has Fragrance I Like | YES | YES | YES |

KEY:
YES = positive experience;
NO = negative experience;
PART = unsatisfactory

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated.

Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A makeup removal and cleansing article, comprising:

a. a water-insoluble substrate;

b. impregnated in the water-insoluble substrate a cleansing composition comprising;

i. at least one branched or linear, liquid alkane with carbon chain length of C11 to C20, each present from about 5% to about 10% by weight of the cleansing composition;

ii. at least one polar emollient with molecular weight of 400 g/mol or less, each present from about 5% to about 10% by weight of the cleansing composition;

iii. at least one polymeric thickener for a water-based system, wherein:

1. acrylates/C10-30 alkyl acrylate crosspolymer, if present in the at least one polymeric thickener, is present from about 0.01% to about 0.05% by weight of the cleansing composition; and 2. carbomer, if present in the at least one polymeric thickener, is present from about 0.01% to about 0.2% by weight of the cleansing composition; and 3. any polymeric thickener species other than the acrylates/C10-30 alkyl acrylate crosspolymer or the carbomer, if present in the at least one polymeric thickener, is present from about 0.01% to about 2% by weight of the cleansing composition;

iv. a total amount of at least one alkylated glycerol ester surfactant present up to about 2% by weight of the cleansing composition, the at least one alkylated glycerol ester surfactant being selected from the group consisting of polyethylene glycol-7 glyceryl cocoate, polyethylene glycol-7 caprylic/capric glycerides, polyethylene glycol-6 caprylic/capric glycerides, disodium cocoyl glutamate and sodium cocoyl glutamate, coco-betaine, caprylyl/capryl glucoside, disodium cocoamphodiacetate, sodium cocoamphoacetate, polyglyceryl-4 caprate, and combinations thereof; and v. water present from about 60% to about 85% by weight of the cleansing composition, wherein the cleansing composition has a viscosity of 400-1,200 cP at room temperature.

2. The makeup removal and cleansing article according to claim 1, wherein the cleansing composition is impregnated onto the water-insoluble substrate in an amount of 250% to 400% by weight of the cleansing composition to the weight of the substrate.

3. The makeup removal and cleansing article according to claim 1, wherein the article is a cosmetic removal wipe that comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations of these.

4. The makeup removal and cleansing article according to claim 1, wherein the cleansing composition is essentially free of silicone.

5. The makeup removal and cleansing article according to claim 1, wherein:

(i) the branched or linear, liquid alkane with carbon chain length of C11 to C20 is selected from isohexadecane, C15-19 alkane, isododecane, undecane, tridecane or a combination thereof, (ii) the at least one polar emollient with molecular weight of 400 g/mol or less is selected from isopropyl myristate, dicaprylyl ether, ethylhexyl palmitate, isopropyl palmitate, cetearyl ethylhexanoate, isononyl isononanoate, isopropyl isostearate, diisopropyl sebacate, coco caprylate/caprate, diisopropyl adipate, or a combination thereof, and the at least one polymeric thickener is selected from carbomer, acrylates/C10-30 alkyl acrylate crosspolymer, polyacrylate crosspolymer-6, microcrystalline cellulose and cellulose gum, xanthan gum, sodium carboxymethyl starch, sclerotium gum and xanthan gum, xanthan gum and *Ceratonia siliqua* (carob) gum, dehydroxanthan gum, hydroxypropyl starch phosphate, sclerotium gum, xanthan gum and sclerotium gum and lecithin and pullulan, or a combination thereof.

6. A makeup removal and cleansing article, comprising:

a. a water-insoluble substrate comprising a cosmetic wipe;

b. impregnated in the water-insoluble substrate a cleansing composition comprising;

i. at least one branched or linear, liquid alkane with carbon chain length of C11 to C20, each present from about 5% to about 10% by weight of the cleansing composition, the at least one branched or linear liquid alkane comprising isohexadecane;

ii. at least one polar emollient with molecular weight of 400 g/mol or less, each present from about 5% to about 10% by weight of the cleansing composition, the at least one polar emollient comprising isopropyl myristate;

iii. polymeric thickener for a water-based system comprising acrylates/C10-30 alkyl acrylate crosspolymer and carbomer present as a combination in a total amount from about 0.13% to about 0.2% by weight of the cleansing composition;

iv. a total amount of at least one alkylated glycerol ester surfactant present up to about 2% by weight of the cleansing composition, the at least one alkylated glycerol ester surfactant comprising polyethylene glycol-7 glyceryl cocoate; and v. water present from about 60% to about 85% by weight of the cleansing composition, wherein the cleansing composition is impregnated onto the water-insoluble substrate in an amount of 250% to 400% by weight of the cleansing composition to the weight of the substrate, and wherein the cleansing composition has a viscosity of 400-1,200 cP at room temperature.

7. The makeup removal and cleansing article according to claim 6, wherein the at least one polymeric thickener for a water-based system consists of acrylates/C10-30 alkyl acrylate crosspolymer and carbomer.

8. The makeup removal and cleansing article according to claim 6, wherein the cleansing composition is impregnated onto the water-insoluble substrate at a weight percent ratio of 1:4 substrate to cleansing composition.

9. A makeup removal and cleansing article, comprising:

a. a water-insoluble substrate;

b. impregnated in the water-insoluble substrate a cleansing composition comprising:

i. at least one branched or linear, liquid alkane with carbon chain length of C11 to C20;

ii. at least one polar emollient with molecular weight of 400 g/mol or less;

iii. at least one polymeric thickener for a water-based system, wherein:

1. acrylates/C10-30 alkyl acrylate crosspolymer, if present in the at least one polymeric thickener, is present from about 0.01% to about 0.2% by weight of the cleansing composition;

2. carbomer, if present in the at least one polymeric thickener, is present from about 0.01% to about 0.2% by weight of the cleansing composition; and 3. any polymeric thickener species other than the acrylates/C10-30 alkyl acrylate crosspolymer or the carbomer, if present in the at least one polymeric thickener, is present from about 0.01% to about 2% by weight of the cleansing composition;

iv. at least one alkylated glycerol ester surfactant, the at least one alkylated glycerol ester surfactant being selected from the group consisting of polyethylene glycol-7 glyceryl cocoate, polyethylene glycol-7 caprylic/capric glycerides, polyethylene glycol-6 caprylic/capric glycerides, disodium cocoyl glutamate and sodium cocoyl glutamate, coco-betaine, caprylyl/capryl glucoside, disodium cocoamphodiacetate, sodium cocoamphoacetate, polyglyceryl-4 caprate, and combinations thereof; and v. water present from about 70% to about 85% by weight of the cleansing composition, wherein a total amount of the alkylated glycerol ester surfactant present is up to about 2% by weight of the cleansing composition, and wherein the cleansing composition has a viscosity of 400-1,200 cP at room temperature.

10. The makeup removal and cleansing article according to claim 9, wherein:

i. each of the at least one branched or linear, liquid alkane with carbon chain length of C11 to C20, is present from about 5% to about 10% by weight of the cleansing composition;

ii. each of the at least one polar emollient with molecular weight of 400 g/mol or less is present from about 5% to about 10% by weight of the cleansing composition; and iii. the total amount of polymeric thickener for water-based system is present from about 0.01% to about 0.2% by weight of the cleansing composition.

11. The makeup removal and cleansing article according to claim 9, wherein:

i. the at least one branched or linear, liquid alkane with carbon chain length of C11 to C20, comprises isohexadecane;

ii. the at least one polar emollient with molecular weight of 400 g/mol or less comprises isopropyl myristate;

iii. the at least one polymeric thickener for water-based system comprises a combination of the carbomer and the acrylate/C10-30 alkyl acrylate crosspolymer; and iv. the at least one alkylated glycerol ester surfactant comprising comprises polyethylene glycol-7 glyceryl cocoate.

12. The makeup removal and cleansing article according to claim 9, wherein the branched or linear, liquid alkane with carbon chain length of C11 to C20 is selected from isohexadecane, C15-19 alkane, isododecane, undecane, tridecane or a combination thereof.

13. The makeup removal and cleansing article according to claim 12, wherein the branched or linear, liquid alkane is present from about 5% to about 10% by weight of the cleansing composition.

14. The makeup removal and cleansing article according to claim 9, wherein the at least one polar emollient with molecular weight of 400 g/mol or less is selected from isopropyl myristate, dicaprylyl ether, ethylhexyl palmitate, isopropyl palmitate, cetearyl ethylhexanoate, isononyl isononanoate, isopropyl isostearate, diisopropyl sebacate, coco caprylate/caprate, diisopropyl adipate, or a combination thereof.

15. The makeup removal and cleansing article according to claim 14, wherein the at least one polar emollient with molecular weight of 400 g/mol or less is present from about 5% to about 10% by weight of the cleansing composition.

16. The makeup removal and cleansing article according to claim 9, wherein:

i. the at least one branched or linear, liquid alkane with carbon chain length of C11 to C20 is selected from isohexadecane, C15-19 alkane, isododecane, undecane, tridecane or a combination thereof;

ii. the at least one polar emollient with molecular weight of 400 g/mol or less is selected from isopropyl myristate, dicaprylyl ether, ethylhexyl palmitate, isopropyl palmitate, cetearyl ethylhexanoate, isononyl isononanoate, isopropyl isostearate, diisopropyl sebacate, coco caprylate/caprate, diisopropyl adipate, or a combination thereof; and iii. the total amount of polymeric thickener for water-based system is selected from microcrystalline cellulose and cellulose gum, xanthan gum, sodium carboxymethyl starch, sclerotium gum and xanthan gum, xanthan gum and *Ceratonia siliqua* (carob) gum, dehydroxanthan gum, hydroxypropyl starch phosphate, sclerotium gum and xanthan gum, Sclerotium gum, xanthan gum and sclerotium gum and lecithin and pullulan, or a combination thereof.

17. The makeup removal and cleansing article according to claim 9, wherein the at least one polymeric thickener consists of a combination of carbomer and acrylate/C10-30 alkyl acrylate crosspolymer and wherein the total amount of polymeric thickener present from about 0.13% to about 0.2% by weight of the cleansing composition.

18. The makeup removal and cleansing article according to claim 9, wherein the at least one polymeric thickener comprises carbomer present from about 0.01% to about 0.2% by weight of the cleansing composition and a polymeric thickener selected from the group consisting of polyacrylate crosspolymer-6, microcrystalline cellulose and cellulose gum, xanthan gum, sodium carboxymethyl starch, sclerotium gum and xanthan gum, and combinations thereof.

19. The makeup removal and cleansing article according to claim 9, further comprising at least one additive, the additive including at least one humectant, at least one preservative, or combinations thereof, the at least one humectant, if present, including glycerin, and the at least one preservative, if present, including hydroxyacetophenone, caprylyl glycol, or combinations thereof, and wherein the cleansing composition is essentially free of silicone.

* * * * *